United States Patent [19]

Pereyre et al.

[11] 4,394,320
[45] Jul. 19, 1983

[54] SYNTHESIS OF STANNIC TETRA MERCAPTIDES

[75] Inventors: Michel Pereyre, Talence; Jean-Claude Pommier, Gradignan, both of France

[73] Assignee: Societe Nationale Elf Aquitaine, France

[21] Appl. No.: 356,820

[22] Filed: Mar. 10, 1982

[30] Foreign Application Priority Data

Mar. 12, 1981 [FR] France ............................. 81 04965

[51] Int. Cl.$^3$ ............................................... C07F 7/22
[52] U.S. Cl. ................................................. 260/429.7
[58] Field of Search ..................................... 260/429.7

[56] References Cited

U.S. PATENT DOCUMENTS 2,726,227 12/1955 Leistner et al. ............. 260/429.7 X
2,888,435 5/1959 Wallace ...................... 260/429.7 X

OTHER PUBLICATIONS

Chemical Abstracts, 16 3077, (1922).
Chemical Abstracts, 49 13012, (1955).
Chemical Abstracts, 54 4271, (1960).

Primary Examiner—Helen M. S. Sneed
Attorney, Agent, or Firm—Ostrolenk, Faber, Gerb & Soffen

[57] ABSTRACT

Process for the preparation of stannic tetra mercaptides in an economic manner through the action of corresponding mercaptans and metallic tin, at a temperature maintained between 15° C. and 200° C.

11 Claims, No Drawings

SYNTHESIS OF STANNIC TETRA MERCAPTIDES

The present invention relates to a new process for the production of stannic mercaptides.

Tetravalent tin mercaptides have a special industrial worth, particularly for the stabilisation of resins containing a halogen, and above all for polyvinyl chloride which is manufactured on a large scale. The interest of tetramercaptides has become, at the present time, that much more pertinent since a new stabilisation process, developed by the applicant, foresees the use of these compounds jointly with crown-ethers, as described in French Patent application No. 79.11248. It is thus important to have an economic maufacturing process of such mercaptides, which allows their obtention in a sufficiently pure state. However, the existing processes do not satisfy industrial requirements. Indeed, the only syntheses known up to now, consist in reacting anhydrous tin tetrachloride $SnCl_4$ with a mercaptide, especially an alkaline or alkaline-earth mercaptide, often produced in situ, the original product being a mercaptan used in the presence of an organic or inorganic base. Thus, according to H. J. BACKER process (Rec. Trav. Chim. 52,916 of 1933 and ibid 53,1101 of 1934)Na Mercaptide is used according to the reaction, $4RSNa + SnCl_4 \rightarrow Sn(SR)_4$. U.S. Pat. No. 2,726,227 describes the preparation of $Sn(SC_{12}H_{25})_4$ by heating $SnCl_4$ with dodecanethiol. The same reaction, but in the presence of an organic base, is described by MEHROTRA and colls, in J. Inorg. Nucl. Chem. 29, 1577 of 1967. According to German Pat. No. 2.302.749, the organic base is ethylene diamine.

The known processes all have different drawbacks. One of the main drawbacks lies in the fact that the process must be operated in several steps, by first isolating the mercaptide of the selected base, especially Na, before causing it to react with stannic chloride. Furthermore, the use of $SnCl_4$ comprises handling difficulties due to the fumes and the corrosion activity of said compound.

Moreover, more or less complicated treatments are necessary to separate the products obtained in order to recover the stannic chloride and organic thioderivative which have not reacted; then, given the relatively low yields, normally lower than 60%, and the high costs of the tin compounds, the recovery of $SnCl_4$, with a view to recycling, is indispensable.

The present invention offers a substantial improvement of the production technique of Sn tetra mercaptides, which overcomes the drawbacks mentioned above. Indeed, it allows a single-step operation, without having to handle a difficult reactant and enables easy separation and re-cycling of the unreacted components.

The new process according to the invention is characterized in that a mercaptan is heated with metallic tin particles, after which the metal which has not reacted is mechanically separated from the reaction medium. The mercaptide thus obtained is separated from the residual mercaptan in the standard way, this separation being carried out, as required, by distillation or precipitation. The process according to the invention applies to the preparation of different mercaptides, especially those of the tetra mercaptides of the $Sn(SR)_4$ type in which R is a hydrocarbon group, able to bear various functions such as for example, a carboxy, hydroxy, carbonyl or other group. More especially, the hydrocarbon radical is an aliphatic or cycloaliphatic radical. Thus, the process according to the invention applies very advantageously to the preparation of tetra mercaptides, in which R is a $C_4$ to $C_{18}$ linear or branched aliphatic chain or again a $C_5$ to $C_{12}$ cycloaliphatic group.

The temperature to which the mercaptan must be heated with metallic tin in order to produce a practicably useful proportion of tetra mercaptides depends on the nature of the mercaptan used, on the fineness of the tin particles, on the stirring speed and on a possible presence of a solvent; in normal conditions, this temperature is most often in the range comprised between 150° C. and 200° C., and more particularly between 170° C. and 190° C.

It is possible to use metallic tin in the form of grains, whose dimensions range between 1 micron and several millimeters in diameter, for example from 1 micron to 5 mm; however, in normal practice, the most advantageous dimensions are in the range comprised between 10 and 500 μm. The speed of the reaction increases with the fineness of the grains. Consequently, the duration of heating is variable, depending on the size of Sn particles and the temperature selected; most frequently this heating is extended to between 6 and 60 hrs.

Although the reaction can be carried out with stochiometric proportions, i.e. with 1 tin atom for 4 moles of mercaptan, corresponding to the theoretical equation $Sn + 4RSH \rightarrow Sn(SR)_4 + 2H_2$, it is preferable to operate with a metal excess, which thus both improves and accelerates the reaction. Therefore, 1 to 4 Sn atoms can be used for 4 moles of mercaptan and, preferably, 1.5 to 3 Sn atoms; given the utmost ease with which the Sn excess can be separated, by simple filtration, from the reaction medium, the use of an excess of metallic powder does not create any difficulty. The yields, with respect to the mercaptan used, are generally of about 50% to 60%, but none of these reactants are lost, since it is very easy to separate and recycle tin, as described herein-above, as well as the original mercaptan whose separation presents no difficulty.

The invention is shown, by non-limitative examples, as follows.

EXAMPLE 1

Preparation of tetra lauryl mercaptide of tin

To 8.1 g lauryl mercaptan $C_{12}H_{25}SH$, (40 mmol), 1.8 g tin, i.e. 15 m.at.g are added in the form of a powder, the particles of which have sizes of between 50 and 200 microns; the mixture is heated to 180° C., under continued stirring, for 44 hours. The solution assumes progressively a yellow colouration which borders on black after 5 to 10 minutes.

At the end of heating and after cooling, the solution sets in block, then pentane is added until dissolution; the obtained solution is filtered so as to separate the non-reacted tin. The filtrate is subjected to evaporation under vacuum by a water driven vacuum pump that gives rise to a white solid precipitation. After three further dissolutions in pentane followed by vacuum precipitation, 5.6 g tetra lauryl mercaptide tin is obtained; this represents a yield of 61% purified product with respect to the original lauryl mercaptan.

The obtained mercaptide $(C_{12}H_{25}S)_4 Sn$, melts at 37° C. and an examination of its magnetic nuclear resonance gives the following results: $RMN^1H$ triplet at 2.70 ppm (—$CH_2S$—); $RMN^{119}Sn$ 142.2 ppm (with respect to tetra methyl tin). Elementary analysis indicates:

|  | C % | H % | Sn % | S % |
|---|---|---|---|---|
| calculated | 62.40 | 10.83 | 12.89 | 13.86 |
| found | 62.78 | 10.45 | 12.60 | — |

EXAMPLE 2

Preparation of tin tetra n.octyl-mercaptide

A mixture of 5.84 g of n.octyl-mercaptan, or 40 mmol, with 1.8 g, (i.e., 15 m. at. g) of tin powder of the same fineness as in Example 1, is heated to 180° C., during 48 h. The viscous liquid thus obtained is dissolved in pentane and the solution is filtered in order to separate the excess tin. After evaporating the pentane with a water driven vacuum pump, the non-reacted octyl-mercaptan is eliminated by distillation under vacuum of 0.1 to 1 mm Hg.

Thus, 4.11 g viscous liquid is recovered, consisting in tin tetra octyl-mercaptide: the yield, with respect to the original mercaptan, is 59%.

An examination of the magnetic nuclear resonnance indicates: RMN$^1$H Triplet at 2.76 ppm (—CH$_2$S—); RMN$^{119}$Sn 144.0 ppm (with respect to tetra methyl-tin).

An elementary analysis shows that although the body obtained is (C$_8$H$_{17}$S)$_4$ Sn

|  | C % | H % | Sn % | S % |
|---|---|---|---|---|
| calculated | 54.93 | 9.73 | 17.02 | 18.31 |
| found | 55.92 | 10.01 | 15.90 | 17.98 |

EXAMPLE 3

Preparation of tin tetra cyclohexyl-mercaptide

A mixture of 4.64 g cyclohexyl-mercaptan, or 40 mmol, with 1.8 g, i.e. 15 m. at. g. powdered tin, is heated to 180° C. during 48 hours.

After heating, pentane is added to the reaction medium, and the solution obtained is filtered so as to separate the excess tin. The pentane is thereafter eliminated by evaporation under vacuum, and a solid white product is obtained. This product is washed several times with methanol and then dried. 2.8 g tin tetra cyclohexyl-mercaptide crystals are obtained, corresponding to a yield of the pure product, with respect to reacted cyclohexyl-mercaptan, of 49%. The tetra mercaptide obtained melts at 58° C. and an examination of its magnetic nuclear resonnance is: gives a large RMN$^1$H band between 2.7 and 3.2 ppm (—CH$_2$S—) RMN$^{119}$Sn 111.9 ppm (with respect to tetra methyl tin).

An elementary analysis shows (C$_6$H$_{11}$S)$_4$ Sn for the product obtained:

|  | C % | H % | Sn % | S % |
|---|---|---|---|---|
| calculated | 49.74 | 7.59 | 22.10 | 20.55 |
| found | 49.78 | 7.75 | 21.65 | 21.77 |

We claim:

1. Process of preparation of stannic tetra mercaptides from corresponding mercaptans comprising the step of heating the mercaptan with metallic tin.

2. Process according to claim 1, wherein the tin is in the form of particles of 1 micron to 5 mm in diameter.

3. Process according to claim 2, wherein said particles are of 10 to 500 microns in diameter.

4. Process according any one of claims 1 to 3, wherein the heating is carried out at a temperature of 150° to 200° C.

5. Process according to claim 4, wherein the heating is carried out at a temperature between 170° to 190° C.

6. Process according to one of the claims 1 to 3, wherein the proportion of tin is from 1 to 4 gram atoms per 4 moles of mercaptan.

7. Process according to one of the claims 1 to 3, wherein the proportion of tin is from 1.5 to 3 gram atoms Sn for 4 moles of mercaptan.

8. Process according to one of the claims 1 to 3, wherein the unreacted tin is separated by filtration in order to be re-used in a fresh operation.

9. Process according to claim 8, wherein the reaction medium is fluidified by addition of a solvent prior to filtration, with the purpose of separating the unreacted tin.

10. Process according to one of claims 1 to 3, wherein the unreacted mercaptan fraction is eliminated from the reaction medium in order to be recycled in a fresh operation.

11. Process according to claim 1 wherein the mercaptan is selected from the group consisting of lauryl mercaptan, n-octyl mercaptan and cyclohexyl mercaptan.

* * * * *